United States Patent [19]

Costantini et al.

[11] Patent Number: 4,918,238

[45] Date of Patent: Apr. 17, 1990

[54] CATALYTIC OXIDATION OF ALKANES INTO ALCOHOL/KETONE MIXTURES

[75] Inventors: Michel Costantini; Jean-Pierre Lecomte, both of Lyons, France

[73] Assignee: Rhone-Poulenc Chimie, Courbevoie, France

[21] Appl. No.: 318,911

[22] Filed: Mar. 3, 1989

[30] Foreign Application Priority Data

Mar. 3, 1988 [FR] France .................................. 88 02987

[51] Int. Cl.$^4$ .............................................. C07C 45/28
[52] U.S. Cl. .................................... 568/342; 568/311; 568/385; 568/803; 568/909.8
[58] Field of Search ............... 568/385, 311, 342, 803, 568/909.8

[56] References Cited

U.S. PATENT DOCUMENTS

| | | | |
|---|---|---|---|
| 3,231,620 | 1/1966 | Cotterill et al. | 568/342 |
| 3,337,635 | 8/1967 | Norton et al. | 568/385 |
| 3,879,467 | 4/1975 | Zajacek | 568/385 |
| 3,928,452 | 12/1975 | Brunie et al. | 568/909.8 |
| 4,203,926 | 5/1980 | Wu et al. | 568/860 |

FOREIGN PATENT DOCUMENTS

| | | | |
|---|---|---|---|
| 2213261 | 8/1974 | France | 568/820 |
| 540370 | 10/1941 | United Kingdom | 568/820 |
| 1041946 | 5/1965 | United Kingdom | 568/342 |

*Primary Examiner*—James H. Reamer
*Attorney, Agent, or Firm*—Burns, Doane, Swecker & Mathis

[57] ABSTRACT

Mixtures of alcohols and ketones are selectively and actively produced by catalytically oxidizing at least one alkane with an organic hydroperoxide, in the presence of a catalytically effective amount of osmium or an osmium compound, notably osmium tetroxide.

19 Claims, No Drawings

CATALYTIC OXIDATION OF ALKANES INTO ALCOHOL/KETONE MIXTURES

BACKGROUND OF THE INVENTION

1. Field of the Invention:

The present invention relates to a process for the catalytic oxidation of alkanes, and, more especially, for the catalytic oxidation of alkanes into mixtures of alcohols and ketones.

2. Description of the Prior Art:

The catalytic oxidation of alkanes by organic hydroperoxides is a reaction known to this art and various catalytic systems have already been proposed for conducting such reaction.

Thus, D. Mansuy et al, in *Angew. Chem. Int. English Edition*, 19. No. 11, pages 909–910 (1980), described the decomposition of cumyl hydroperoxide in cyclohexane at 20° C., in which the catalyst was the Os(TPP)(CO)(pyridine) complex wherein TPP designates tetraphenylporphyrin. However, the yield of desired compounds (cyclohexanol and cyclohexanone) was insignificant and the activity of the catalyst was very low. Moreover, if its structure is modified at 20° C., experiments have shown that it is destroyed at a higher temperature. Under these conditions, development of such a technique on an industrial scale using a complex of prohibitive cost is not realistic.

Also, published French Patent Application No. 2,559,154 describes, in particular, the oxidizing deperoxidation of t-butyl and cumyl hydroperoxides in cyclohexane or octane in which the catalyst is a cobalt complex which notably comprises at least one ligand having a bis(2'-pyridylimino)isoindoline skeleton. It is also reported in Example 27 of the '154 application that the compound Co(Oct)$_2$, the structure of which is simpler and which does not include a ligand of the above indicated type, only exhibits very poor efficiency. The '154 application suggests the possible replacement of cobalt, the central metal in the complexes in question, by any other metal of Group VIII, with osmium being one of the possibilities considered. However, the ligands in question are relatively difficult to prepare and the efficiency of the various complexes tested in the reaction under consideration, the principal metal of which being cobalt, remains poor. Development of such technique on an industrial scale is hence also not realistic.

SUMMARY OF THE INVENTION

Accordingly, a major object of the present invention is an improved process for the catalytic oxidation of alkanes by organic hydroperoxides which avoids those disadvantages and drawbacks to date characterizing the state of this art, which is more efficient and which permits the use of catalysts that are more stable to heat, more readily available and which can be recycled, if necessary.

Briefly, the present invention features an improved process for the oxidation of alkanes by organic hydroperoxides into mixtures of alcohols and ketones, such improved process being carried out at a temperature above 20° C. and in the presence of a catalytically effective amount of osmium or of a compound of osmium.

DETAILED DESCRIPTION OF THE PREFERRED EMBODIMENTS OF THE INVENTION

More particularly according to the present invention, by the term "alkanes", the principal substrates in the process of the invention, are intended saturated hydrocarbons corresponding to the formula (I) below:

in which R is a linear or branched chain alkyl radical having from 1 to 30 carbon atoms; a cycloalkyl radical having from 3 to 12 ring carbon atoms, optionally substituted by one or more alkyl radicals containing up to 4 carbon atoms; a polycycloalkyl radical having from 2 to 5 rings, each of which having from 3 to 12 ring carbon atoms; or an alkyl- or cycloalkylaromatic radical having from 7 to 30 carbon atoms.

Preferably, R is a linear or branched chain alkyl radical having from 1 to 12 carbon atoms; a cycloalkyl radical having from 5 to 12 ring carbon atoms; an alkylbenzene radical, in which the alkyl moiety contains up to 4 carbon atoms; or a cycloalkylbenzene radical, in which the cycloalkyl moiety contains 5 to 8 carbon atoms.

Exemplary of suitable oxidizable alkanes according to this invention are methane, ethane, propane, isobutane, isopentane, butane, hexane, octane, cyclopentane, cumene, toluene, tetralin, decalin, cyclododecane and pinane.

The process of the present invention also requires an organic hydroperoxide. Such compounds may be represented by the general formula (II) below:

in which R$_1$, R$_2$ and R$_3$, which may be identical or different, are each a hydrogen atom; a linear or branched chain alkyl radical having from 1 to 30 carbon atoms; a cycloalkyl radical having from 3 to 12 carbon atoms; an alkyl- or cycloalkylaromatic radical having from 7 to 30 carbon atoms; or an aryl radical, optionally substituted by one or two alkyl radicals containing up to 4 carbon atoms, or aryl radicals having from 6 to 20 carbon atoms; with the proviso that two of the R$_1$, R$_2$ and R$_3$ radicals may together form a single divalent alkylene radical containing from 4 to 10 carbon atoms.

Preferably, R$_1$, R$_2$ and R$_3$, which may be identical or different, are each an alkyl radical having from 1 to 4 carbon atoms; or a phenyl radical; with the proviso that two of the R$_1$, R$_2$ and R$_3$ radicals may together form, with the carbon atoms from which they depend, a single divalent radical constituting a cyclohexyl or cyclooctyl radical; and with the further proviso that one of R$_1$, R$_2$ and R$_3$ may be a hydrogen atom.

Representative organic hydroperoxides according to the present invention are tertiary-butyl hydroperoxide, cumyl hydroperoxide, cyclohexyl hydroperoxide and ethylbenzene hydroperoxide.

As indicated above, a final product mixture is obtained according to the present invention containing at least the alcohol and at least the ketone corresponding to the alkane used as the starting material, or to the alkyl moiety of the aralkyl substrate. Thus, from cyclohexane a mixture of cyclohexanol and cyclohexanone will be obtained, which are useful intermediates in various manufacturing processes (adipic acid, caprolactam), a mixture commonly referred to as OLONE. In the same manner, starting from ethylbenzene, a mixture of 1-phenylethanol and acetophenone will be obtained, useful for the production of styrene.

The process of this invention also requires the presence of osmium or of a compound of osmium.

Any source of osmium may be used according to the present invention. The osmium may, indeed, be in metallic form, if necessary, finely divided or deposited onto a support such as activated charcoal. Also suitable are compounds of osmium in which the osmium has a zero state of oxidation, such as triosmium dodecacarbonyl. Inorganic compounds of osmium may also be used, in which the osmium exhibits any state of oxidation from 2 to 8. Examples of such compounds are: OsO, $Os_2O_3$, $OsO_2$, $OsO_4$, $OsCl_3$, $K_2OsO_4$, $NaOsF_6$, $OsOCl_4$, $K_2OsO_4(OH)_2$, $OsCl_4$ and $OsOF_5$.

It is also possible to use organic compounds of osmium, or osmium complexes such as tetracyclohexyl osmium, tetra(cyclohexyloxy) osmium or the Os(TPP)-(CO)(pyridine) complex, and particularly, complexes comprising ligands having a high nitrogen atom density (e.g., tri- or tetranitrogenated) like the ligands exhibiting the tetraphenylporphyrin skeleton. Most of the complexes in question release an inorganic form of osmium, in situ, under the conditions of the reaction, either by degradation of the ligands or by decomplexation.

Preferably, the form of osmium used will be any one of the following:

Os/C, $Os_3(CO)_{12}$, OsO, $Os_2O_3$, $OsO_2$, $OsO_4$ and $OsCl_3$.

Osmium tetroxide is particularly suitable for carrying out the present invention.

The amount of osmium to be used is not critical and may vary over wide limits. For good performance of the invention, it will be at least $10^{-5}$ mole of osmium per mole of hydroperoxide. There is no observable advantage in exceeding an amount of $10^{-1}$ mole of osmium per mole of hydroperoxide. This amount ranges from $10^{-2}$ to $10^{-5}$ mole of osmium per mole of hydroperoxide.

The molar ratio of hydroperoxide to alkane may also vary over wide limits; a minimum of 0.001 molar % is however recommended to enable an appreciable degree of conversion of the alkane to be effected. This ratio may be as high as 100%. Preferably, this ratio ranges from 0.01% to 25%.

The reaction may of course be conducted using a large excess of alkane, which also then serves as diluent. It is also possible to operate in the presence of diluents or solvents that are not oxidizable under the conditions of the reaction, such as benzene and chlorobenzene.

In a preferred embodiment of the present process, the reaction is conducted in the presence of a diluent selected from among the saturated alcohols, the saturated diols and polyols, water and mixtures thereof.

The saturated alcohols that are suitable for carrying out the process of this invention have the general formula (III) below:

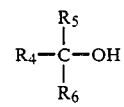

(III)

in which $R_4$, $R_5$ and $R_6$, which may be identical or different, are each a hydrogen atom; a linear or branched chain alkyl radical having from 1 to 30 carbon atoms; a cycloalkyl radical having from 3 to 12 carbon atoms; an alkyl- or cycloalkylaromatic radical having from 7 to 30 carbon atoms; or an aryl radical, optionally substituted by one or two alkyl radicals containing up to 4 carbon atoms, or aryl radicals having from 6 to 20 carbon atoms; with the proviso that two of the $R_4$, $R_5$ and $R_6$ radicals may together form a single divalent alkylene radical containing 4 to 10 carbon atoms; and three of the $R_4$, $R_5$ and $R_6$ radicals may together form a single trivalent polycyclic radical containing 6 to 20 carbon atoms.

The saturated diols and polyols comprise a skeleton of general formula (III) above, onto which at least one supplementary hydroxyl group is introduced and, preferably, up to 6 supplementary hydroxyl groups.

Exemplary such diluents are methanol, ethanol, isopropanol, tertiary butanol, 1-hexanol, 1-octanol, 1-dodecanol, cyclohexanol, dimethylphenylcarbinol, ethylene glycol, 1,3-propanediol and 2,4-dimethyl-2,4-dihydroxypentane.

The saturated alcohol used as the diluent may of course be of the same nature as or of a different nature from the alcohol produced in the reaction. It is also possible to use as the diluent a mixture containing an alcohol endogenous to the reaction medium and an alcohol exogenous thereto.

It is preferred to use water or a saturated alcohol of formula (III) above in which $R_4$, $R_5$ and $R_6$, which may be identical or different, are each linear alkyl radicals having 1 to 4 carbon atoms, or a hydrogen atom.

Tertiary butanol is more particularly suitable for carrying out the subject process.

As indicated above, it is possible to use mixtures of diluents and in particular a mixture of saturated alcohol (or saturated diol or polyol) and water. Good results are in particular obtained with a mixture of tertiary butanol and water.

The amount of diluent or mixture of such diluents may vary over wide limits: an appreciable influence is observed when this amount is on the order of 2% by weight of alkane to be oxidized. No positive effect is observed when this amount exceeds 200% by weight of alkane. Good results are obtained using an amount of diluent(s) ranging from 2% to 100% by weight of the alkane.

When a mixture of alcohol and water is used, the amount of water is not critical; it may also vary over wide limits.

Depending on the precise water content of the reaction medium, the precise nature of the alcohol and/or the alkane, the presence of a single phase or of two phases may be observed: an organic phase and an aqueous phase. The presence of such a two-phase system, particularly upon completion of the reaction, is another advantage of the process of the present invention to the extent that the products of oxidation and the unreacted alkane may be separated by decantation or extraction from the catalyst system, the larger part of which is found in the aqueous phase upon completion of the reaction. The residual aqueous phase may easily be used, if necessary after treatment, to catalyze a new oxidation reaction.

It has also been observed that it is advantageous to operate in the presence of a buffer mixture such that the pH of the aqueous phase is maintained at a value of from 2 to 14. To this end, it is particularly advantageous that one or more of the following compounds be added to the reaction medium: alkali metal hydroxides, inorganic or organic oxyacids and their alkali or alkaline earth metal salts and in particular, acetic acid and its salts, phosphoric acid and its salts, and boric acid and its salts.

The reaction temperature depends on the precise nature of the alkane to be oxidized and that of the organic hydroperoxide. It generally ranges from 50° to 180° C., and preferably from 70° to 150° C.

The reaction is carried out at atmospheric pressure or, if necessary, at a pressure above atmospheric pressure such as to maintain the constituents of the reaction mixture in the liquid phase.

The reaction time (or residence time) generally ranges from a few minutes to several hours and may be adjusted, taking account of the objectives of production, the amount of catalyst and the other reaction parameters.

Upon completion of the reaction, the final products may be recovered by any appropriate means, e.g., by distillation.

In order to further illustrate the present invention and the advantages thereof, the following specific examples are given, it being understood that same are intended only as illustrative and in nowise limitative.

In said examples, the following conventions are used:

DC designates: the degree of conversion of the organic hydroperoxide involved in the reaction.

YD designates: the yield of a product (or mixture of products) in relation to the converted hydroperoxide.

YD (OLONE): designates the yield of mixture of cyclohexanol and cyclohexanone.

YD (OL) designates the yield of cyclohexanol.

YD (8-OL): designates the yield of cyclooctanol.

YD (8-ONE): designates the yield of cyclooctanone.

YD (8-OLONE): designates the yield of mixture of cyclooctanol and cyclooctanone.

YD (DMPC): designates the yield of dimethylphenylcarbinol.

YD (A+D): designates the yield of mixture of acetophenone and dimethylphenylcarbinol.

CHPO: designates cumyl hydroperoxide.

CHHPO: designates cyclohexyl hydroperoxide.

T: designates temperature.

EXAMPLE 1

Into a 20 ml Carius type glass tube, the following materials were charged at room temperature:
(i) $OsO_4$ (28 mg, 0.1 mmol) in solution in cyclohexane;
(ii) cyclohexane deoxygenated with argon (5 ml, 46 mmol); and
(iii) cyclohexyl hydroperoxide (100 mg, 0.9 mmol).

A magnetic bar was added and the tube was purged with a current of argon. The tube was cooled with dry ice, and sealed. The whole was then heated to 100° C. for 22 hours. The reaction mass was then analyzed iodometrically and by gas phase chromatography.

99% of the cyclohexyl hydroperoxide had been converted:
YD (OL)=89%
YD (ONE)=46%
YD (OLONE)=135%

EXAMPLE 2

Into a 1.9 ml glass vial, sealed with a Teflon ®-coated cap, the following materials were charged:
(i) osmium as a 5% deposit on charcoal (0.48 mg) (24 micrograms of osmium. i.e. $1.26.10^{-4}$ mmol of osmium);
(ii) cyclooctane (0.82 g, 7.32 mmol);
(iii) orthodichlorobenzene (10.5 mg) (standard for GPC);
(iv) 99% cymyl hydroperoxide (CHPO) (11.5 mg, 0.75 mmol).

The vial was immersed in an oil bath thermostatted at 100° C. for 17 hours, the reaction medium being stirred by a magnetic bar.

The degree of conversion of the CHPO was 100% and the results obtained were as follows:
YD (8-OL)=18%
YD (8-OLONE)=38%
YD (DMPC)=80%
YD (A+D)=84.5%

EXAMPLE 3

Into a glass reactor of 200 ml capacity, equipped with a descending condenser, a gas inlet and outlet, a septum stopper, stirred by a magnetic bar and purged with argon, the following materials were introduced:
(i) cyclooctane (21 g, 187 mmol);
(ii) tertiary butanol (8 g, 108 mmol);
(iii) 1M $H_3BO_3$/NaOH buffer (pH=12.7) (2.5 ml);
(iv) osmium in the form of triosmium dodecacarbonyl ($6.7.10^{-4}$ mmol) in solution in chlorobenzene (0.20 mg of solution).

The reaction medium was heated to 80° C., then cumyl hydroperoxide (CHPO) (0.79 g, 5.5 mmol) was injected through the septum stopper over the course of 20 seconds.

The degree of conversion of the CHPO was monitored iodometrically; at the end of the test the reaction mass was homogenized by addition of tert-butanol and analyzed by gas phase chromatography.

After 3.1 hours of reaction at temperature, the results were as follows:
DC (CHPO)=97%
YD (8-OL)=56.6%
YD (8-ONE)=8.1%
YD (A+D)=97.6%

EXAMPLES 4 to 8

Into a glass tube and following an operating procedure analogous to that described in Example 1, a series of tests was carried out on a charge containing:
(i) cyclohexane (5.1 g, 60.7 mmol);
(ii) 96% cyclohexyl hydroperoxide (0.40 g, 3.3 mmol);
(iii) tertiary butanol;
(iv) osmium tetroxide in solution in cyclohexane.

The duration of each test was 24 h.

The particular conditions and the results obtained are reported in Table I below:

TABLE I

| Example | OsO4/CHHPO mol/mol | t-BuOH* (%) | T °C. | DC (%) | YD(OL) (%) | YD(OLONE) (%) |
|---|---|---|---|---|---|---|
| 4 | $1.9 \cdot 10^{-4}$ | 21 | 130 | 92.3 | 128.2 | 153.8 |
| 5 | $1.3 \cdot 10^{-4}$ | 20 | 150 | 100 | 108.1 | 133.8 |
| 6 | $1.5 \cdot 10^{-4}$ | 102 | 150 | 100 | 111.9 | 129.0 |
| 7 | $47 \cdot 10^{-4}$ | 22 | 120 | 100 | 132.7 | 151.6 |
| 8 | $47 \cdot 10^{-4}$ | 86 | 120 | 100 | 132.8 | 146.5 |

*t-BuOH: weight ratio of t-BuOH to cyclohexane.

EXAMPLES 9 and 10

Into a 1.9 ml glass vial, sealed with a Teflon ®-coated cap, the following materials were charged:
(i) cyclohexane (1.10 g, 13.1 mmol);
(ii) 96% cyclohexyl hydroperoxide (0.0144 g, 0.124 mmol);
(iii) osmium tetroxide ($1.01.10_{-4}$ mmol) in solution in cyclohexane;
(iv) dichlorobenzene (0.082 g) (standard for HPLC);
(v) in Example 9 only, tertiary butanol (0.047 g, 0.632 mmol).

The vial was immersed in an oil bath thermostatted at 120° C. for 20 hours. The results and particular conditions are reported in Table II below. The degree of conversion of the CHHPO was 100% in both cases.

TABLE II

| Example | OsO4/CHPO mol/mol | t-BuOH | YD(OL) (%) | YD(OLONE) (%) |
|---|---|---|---|---|
| 9 | $8.14 \cdot 10^{-4}$ | NO | 134 | 159 |
| 10 | $8.14 \cdot 10^{-4}$ | YES | 161 | 173 |

EXAMPLES 11 to 13

In the reactor and following the operating procedure analogous to that described for Example 3, a series of tests was carried out, it being noted that the reaction mass was not homogenized at the end of the tests, on a charge containing:
(i) cyclooctane (30 g, 268 mmol);
(ii) t-butanol (7.7 g, 104 mmol);
(iii) deionized water (0.12 g, 6.7 mmol);
(iv) osmium tetroxide in solution in cyclooctane, the amount of which is indicated in Table III below:

The temperature having been raised to 80° C., the following was injected over the course of 20 seconds:
99% cumyl hydroperoxide (CHPO) (1.6 g, 10.4 mmol).

The results obtained at the end of 5 hours of reaction are also reported in Table III below, the degree of conversion of CHPO being 100% in all cases.

TABLE III

| Example | OsO4/CHPO mol/mol | YD (8-OL) (%) | YD (8-OLONE) (%) | YD (DMPC) (%) | YD (A + D) (%) |
|---|---|---|---|---|---|
| 11 | $8.8 \cdot 10^{-2}$ | 46 | 77 | 94 | 100 |
| 12 | $7.9 \cdot 10^{-3}$ | 54 | 78 | 93 | 100 |
| 13 | $8.4 \cdot 10^{-5}$ | 75 | 81.8 | 92 | 100 |

EXAMPLES 14 to 18

In the reactor and following the operating procedure analogous to that described for Example 3, a series of tests was carried out, it being noted that the reaction mass was not homogenized at the end of the tests, on a charge containing:
(i) cyclooctane (30 g, 268 mmol);
(ii) osmium tetroxide ($8.4.10^{-4}$ mmol) in solution in cyclohexane and, if necessary:
(iii) tert-butanol and
(iv) deionized water.

The temperature having been raised to 80° C., cumyl hydroperoxide (1.6 g, 10.4 mmol) was injected over the course of 20 seconds. (The reaction medium was homogeneous).

The particular conditions and the results obtained are reported in Table IV below, the degree of conversion of CHPO being 100% in all cases.

TABLE IV

| Example | t-BuOH (*) (% wt) | H2O (*) (% wt) | Duration (h) | YD (8-OL) (%) | YD (8-OLONE) (%) | YD (DMPC) (%) | YD (A + D) (%) |
|---|---|---|---|---|---|---|---|
| 14 | 0 | 0 | <1.5 | 26.3 | 46.8 | 88.2 | 92.2 |
| 15 | 2.7 | 0 | <1 | 40.4 | 55.1 | 89.3 | 94.2 |
| 16 | 2.8 | 0.043 | 1.5 | 45.4 | 59.1 | 91.2 | 95.9 |
| 17 | 25.4 | 0 | 4 | 72.0 | 79.7 | 92.8 | 100 |
| 13 | 26 | 0.4 | 5.0 | 75.0 | 81.8 | 91.9 | 100 |
| 18 | 100 | 0 | 5.0 | 76.8 | 82.7 | 85.7 | 100 |

(*) Weight ratio relative to cyclooctane

EXAMPLE 19

Example 17 above was repeated, but replacing the t-butanol by an identical amount of isopropanol.
The results obtained were as follows:
DC (CHPO)=100%
YD (8-OL)=55.8%
YD (8-OLONE)=58.8%
YD (DMPC)=94.2%
YD (A+D)=100%

EXAMPLE 20

Example 17 above was repeated, but replacing the t-butanol by an identical amount of methanol.
The results obtained were as follows:
DC (CHPO)=100%
YD (8-OL)=60%
YD (8-OLONE)=66%
YD (DMPC)=95%

YD (A+D)=99%

EXAMPLE 21

Following the operating procedure described in Examples 11 to 13, the following materials were charged:
(i) cumene (30 g, 250 mmol);
(ii) osmium ($7.0.10^{-4}$ mmol) in the form of osmium tetroxide in solution in cyclohexane.

The temperature having been raised to 100° C., 99% cumyl hydroperoxide (CHPO) (1.71 g, 11.2 mmol) was injected over the course of 20 seconds. After 2 h, 30 min., the temperature Was increased to 130° C. The mixture was analyzed after the reaction had proceeded for 6 h, 20 min. The results were as follows:
DC (CHPO)=98%
YD (DMPC)=115%
YD (A+D)=165%

EXAMPLE 22

Into a 1.9 ml glass vial, sealed with a Teflon ®-coated cap, the following materials were charged:
(i) n-hexane (0.659 g, 7.65 mmol);
(ii) 99% cumyl hydroperoxide (0.0072 g, 0.047 mmol);
(iii) osmium tetroxide ($7.72.10^{-5}$ mmol) in solution in cyclohexane;
(iv) orthodichlorobenzene (0.0074 g) (standard for GPC);
(v) tert-butanol (0.234 g, 3.15 mmol).

The vial was immersed in an oil bath thermostatted at 120° C. for 18 hours.

The results obtained were as follows:
YD (hexanol+2-hexanone)=1.5%
YD (3-hexanone)=1.1%
YD (I-hexanol)=1.8%
YD (2-hexanol)=29.5%
YD (30hexanol)=25.3%
YD (hexanol+hexanone)=59.2%
YD (DMPC)=71%
YD (A+D)=100%

EXAMPLES 23 to 26

Into a 1.9 ml glass vial, sealed with a Teflon ®-coated cap, the following materials were charged:
(i) cyclohexane (0.755 g, 8.95 mmol);
(ii) 99% cumyl hydroperoxide (0.025 g, 0.163 mmol);
(iii) osmium tetroxide ($3.8.10^{-5}$ mmol) in solution in cyclohexane;
(iv) tert-butanol.
(The medium was homogeneous).

The vial was immersed in an oil bath thermostatted at 100° C. for 40 hours.

The degree of conversion of CHPO was 100%.

The particular conditions and the results obtained are reported in Table V below:

TABLE V

| Example | t-BuOH (*) (% wt) | YD (OL) (%) | YD (OLONE) (%) | YD (DMPC) (%) | YD (A + D) (%) |
|---|---|---|---|---|---|
| 23 | 0 | 70.2 | 84.5 | 91.4 | 97.1 |
| 24 | 3.3 | 84.5 | 94.1 | 95.0 | 100 |
| 25 | 23 | 92.5 | 97.9 | 90.8 | 100 |
| 26 | 63 | 88.3 | 93.0 | 81.5 | 100 |

(*) weight ratio relative to cyclohexane.

EXAMPLE 27

In the vial and following the operating procedure described for Examples 23 to 26, a test was carried out on a charge of:
(i) cyclooctane (0.800 g, 7.15 mmol);
(ii) 99% cumyl hydroperoxide (0.034 g, 0.226 mmol);
(iii) osmium tetroxide ($1.9.10^{-5}$ mmol) in solution in cyclohexane;
(iv) 2,4-dimethyl-2,4-dihydroxypentane (0.022 g, 0.166 mmol);

The degree of conversion of the CHPO was 100%.
YD (8-OL)=47.7%
YD (8-OLONE)=59.5%
YD (DMPC)=86.1%
YD (A+D)=92.2%

EXAMPLE 28

Example 27 above was repeated with these differences, that a molar equivalent quantity of osmium trichloride in solution in tert-butanol is charged instead of the tetroxide, and tert-butanol (640 mg, 7.6 mmol) instead of the diol.

The degree of conversion of the CHPO was 100%.
YD (8-OL)=68.6%
YD (8-OLONE)=74.4%
YD (A+D)=92.0%

EXAMPLES 29 to 33

In the reactor and following the operating procedure of Example 3, a series of tests was carried out by injecting, in each case, 99% cumyl hydroperoxide (0.79 g, 5.15 mmol) over the course of 20 seconds onto a charge containing:
(i) cyclooctane (21 g, 187 mmol);
(ii) osmium tetroxide, the precise amount of which is given in Table VI below;
(iii) an aqueous phase (2.5 ml); and, if necessary,
(vi) t-butanol (8.0 g, 108 mmol),
and maintained at 80° C.

Aqueous phase (PA1) comprised deionized water.
Aqueous phase (PA2) comprised a molar solution of the $H_3BO_3$/NaOH buffer in deionized water (pH=12.7).
Aqueous phase (PA3) comprised a molar solution of the $CH_3COOH$/NaOH buffer in deionized water (pH=5.3).

The particular conditions and the results obtained are reported in Table VI below:

TABLE VI

| Example | $OsO_4$/CHPO mol/mol | t-BuOH | (*) | Duration (h) | DC (CHPO) (%) | YD (8-OL) (%) | YD (8-OLONE) (%) |
|---|---|---|---|---|---|---|---|
| 29 | $1.12 \cdot 10^{-3}$ | YES | PA1 | 0.5 | 98 | 64.7 | 66.7 |
| 30 | $1.10 \cdot 10^{-4}$ | YES | PA1 | 7.0 | 33 | nd | nd |
| 31 | $1.10 \cdot 10^{-4}$ | YES | PA2 | 3.0 | 97 | 59.5 | 67.7 |
| 32 | $1.10 \cdot 10^{-4}$ | NO | PA2 | 5.2 | 99.7 | 20.4 | 28.1 |

TABLE VI-continued

| Example | OsO4/CHPO mol/mol | t-BuOH | (*) | Duration (h) | DC (CHPO) (%) | YD (8-OL) (%) | YD (8-OLONE) (%) |
|---|---|---|---|---|---|---|---|
| 33 | $1.60 \cdot 10^{-3}$ | YES | PA3 | 8.0 | 98.3 | 82.7 | 86.1 |

(*) nature of the aqueous phase used
nd: not determined

EXAMPLE 34

Into a glass reactor equipped with a condenser, a magnetic bar stirrer and an overflow to limit the reaction mass to 72 ml, the following materials were introduced:
(i) Cyclohexylhydroperoxide, 96% : 0.351 g (2.9 m.mol);
(ii) Cyclohexanone: 0.482 g (4.91 m.mol);
(iii) Cyclohexanol: 3.194 g (31.9 m.mol);
(iv) Cyclohexane: 54 g
(v) $OsO_4$ in cyclohexane solution: 0.0112 g (0.044 m.mol).

The reaction mixture was stirred and heated under reflux (81° C.). After ten minutes, the mass had a black color. The following were injected simultaneously via teflon tubes:
$OsO_4$ in cyclohexane solution at 1.00 m.mol/1:6.91 g/h (8.9 micromol/h);
Cyclohexylhydroperoxide in cyclohexane solution at 6% by wt: 414 m.mol/: 117 g/h (60.7 m.mol/h).

The reflux was maintained by heating.
After two hours of operation, a steady state was reached. The flow exiting via the overflow was then collected and analyzed.
Molar ratio CHHPO introduced/osmium introduced: 6974
Reaction time: 26.5 minutes
DC (CHHPO): 99.2% (Residual CHHPO/cyclohexane=$3.5 \times 10_{-4}$)
Activity of the osmium: 4.3 catalytic cycles per second
YD (6-ONE): 30%
YD (6-OL): 105.5%
YD (6-OLONE): 135.5%

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the production of a mixture of alcohols and ketones, comprising catalytically oxidizing at least one hydrocarbon with an organic hydroperoxide, at a temperature above 20° C., in the presence of a catalytically effective amount of osmium or an osmium compound.

2. The process as defined by claim 1, said at least one hydrocarbon having the general formula (I).

$$RH \qquad (I)$$

in which R is a linear or branched chain alkyl radical having from 1 to 30 carbon atoms; a cycloalkyl radical having from 3 to 12 ring carbon atoms, or a substituted such radical bearing one or more lower alkyl substituents containing up to 4 carbon atoms; a polycycloalkyl radical having from 2 to 5 ring members, each of which having from 3 to 12 carbon atoms: or an alkyl- or cycloalkylaromatic radical having from 7 to 30 carbon atoms.

3. The process as defined by claim 1, said organic hydroperoxide having the general formula (II):

in which $R_1$, $R_2$ and $R_3$, which may be identical or different, are each a hydrogen atom; a linear or branched chain alkyl radical having from 1 to 30 carbon atoms; cycloalkyl radical having from 3 to 12 carbon atoms; a alkyl- or cycloalkylaromatic radical having from 7 to 30 carbon atoms; or an aryl radical or substituted such radical bearing one or two lower alkyl substituents containing up to 4 carbon atoms, or aryl substituents having from 6 to 20 carbon atoms; with the proviso that two of $R_1$, $R_2$ and $R_3$ may together form a single divalent alkylene radical having from 4 to 10 carbon atoms.

4. The process as defined by claim 2, wherein said alkane having the formula (I), is a linear or branched chain alkyl radical having from 1 to 12 carbon atoms; a cycloalkyl radical having from 5 to 12 ring carbon atoms; an alkylbenzene radical in which the alkyl moiety contains up to 4 carbon atoms; or a cycloalkylbenzene radical in which the cycloalkyl radical contains 5 to 8 carbon atoms.

5. The process as defined by claim 3, wherein said organic hydroperoxide having the formula (II), $R_1$, $R_2$ and $R_3$, which may be identical or different, are each an alkyl radical having from 1 to 4 carbon atoms; or a phenyl radical; with the proviso that two of the $R_1$, $R_2$ and $R_3$ radicals may together form, with the carbon atom from which they depend, a cyclohexyl or cyclooctyl radical; and with the further proviso that one of $R_1$, $R_2$ or $R_3$ may be a hydrogen atom.

6. The process as defined by claim 1, carried out in the presence of a diluent which comprises a saturated alcohol, saturated diol or polyol, water or mixture thereof.

7. The process as defined by claim 6, said diluent comprising an alcohol of the formula (III):

in which $R_4$, $R_5$ and $R_6$, which may be identical or different, are each a hydrogen atom; linear branched chain alkyl radical having from 1 to 30 carbon atoms; a cycloalkyl radical having from 3 to 12 carbon atoms; an alkyl- or cycloalkylaromatic radical having from 7 to 30 carbon atoms; or an aryl radical or substituted such radical bearing one or two lower alkyl substituents containing up to 4 carbon atoms, or aryl substituents having from 6 to 20 carbon atoms; with the proviso that two of $R_4$, $R_5$ and $R_6$ may together form a single divalent alkylene radical having from 4 to 10 carbon atoms; and three of the $R_4$, $R_5$ and $R_6$ radicals may together form a single trivalent polycyclic radical having from 6 to 20 carbon atoms.

8. The process as defined by claim 7, wherein said alcohol having the formula (III), $R_4$, $R_5$ and $R_6$, which may be identical or different, are each a linear alkyl radical having from 1 to 4 carbon atoms, or a hydrogen atom.

9. The process as defined by claim 7, wherein the alcohol comprises from 2% to 200% by weight of the alkane.

10. The process as defined by claim 6, carried out in the presence of a mixture of an alcohol and water.

11. The process as defined by claim 7, said alcohol comprising tert-butanol.

12. The process as defined by claim 1, wherein the amount of osmium ranges from $10^{-2}$ to $10^{-5}$ mole per mole of the hydroperoxide.

13. The process as defined by claim 1, wherein the organic hydroperoxide comprises from 0.001 to 100% (molar) of the alkane.

14. The process as defined by claim 1, carried out at a reaction temperature of from 70° to 150° C.

15. The process as defined by claim 1, wherein the osmium or osmium compound comprises metallic osmium, metallic osmium deposited onto a support, an inorganic compound of osmium, or an organic complex of osmium which releases an inorganic form of osmium in the reaction medium.

16. The process as defined by claim 1, wherein the osmium or osmium compound comprises osmium tetroxide.

17. The process as defined by claim 1, wherein said at least one alkane comprises cyclohexane.

18. The process as defined by claim 1, wherein said hydroperoxide comprises cyclohexyl hydroperoxide.

19. The process as defined by claim 1, carried out in the liquid phase.

* * * * *